United States Patent [19]

Haagensen

[11] Patent Number: 5,641,907
[45] Date of Patent: Jun. 24, 1997

[54] APPARATUS FOR EXAMINING CARCASSES WITH AN ULTRASOUND TRANSDUCER

[75] Inventor: Peter Haagensen, Red Hill, Pa.

[73] Assignee: SFK-Technology A/S, Søborg, Denmark

[21] Appl. No.: 424,405

[22] PCT Filed: Oct. 28, 1993

[86] PCT No.: PCT/DK93/00347

§ 371 Date: Jun. 26, 1995

§ 102(e) Date: Jun. 26, 1995

[87] PCT Pub. No.: WO94/10562

PCT Pub. Date: May 11, 1994

[30] Foreign Application Priority Data

Oct. 28, 1992 [DK] Denmark ................. 1316/92

[51] Int. Cl.⁶ ................. A61B 8/00; G01N 29/26; A22B 7/00
[52] U.S. Cl. ................. 73/620; 73/625; 73/628; 128/660.07; 128/660.01
[58] Field of Search ................. 73/626, 620, 602, 73/625, 628; 128/660.07, 660.06, 660.01; 364/413.25

[56] References Cited

U.S. PATENT DOCUMENTS

| | | | |
|---|---|---|---|
| 4,030,343 | 6/1977 | Lund et al. | 73/626 |
| 4,208,915 | 6/1980 | Edwards | 73/620 |
| 4,785,817 | 11/1988 | Stouffer | 128/660.07 |
| 5,079,951 | 1/1992 | Raymond et al. | 73/602 |
| 5,140,988 | 8/1992 | Stouffer et al. | 128/660.01 |
| 5,208,747 | 5/1993 | Wilson et al. | 128/660.07 |
| 5,353,796 | 10/1994 | Schroeder et al. | 128/660.01 |

FOREIGN PATENT DOCUMENTS

WO83/02053  6/1983  WIPO.

Primary Examiner—Hezron E. Williams
Assistant Examiner—Rose M. Miller
Attorney, Agent, or Firm—Finnegan, Henderson, Farabow, Garrett & Dunner

[57] ABSTRACT

Apparatus for examining carcasses on a slaughter line, in which an ultrasound transducer comes into contact with a surface of the carcasses. The ultrasound transducer is adapted to be mounted immovably on a stationary frame of the slaughter line so that as the carcass transport mechanism of the slaughter line moves the carcasses across the ultrasound transducer, the carcasses rest on the ultrasound transducer with a considerable part of their weight.

9 Claims, 4 Drawing Sheets

APPARATUS FOR EXAMINING CARCASSES WITH AN ULTRASOUND TRANSDUCER

BACKGROUND OF THE INVENTION

The invention concerns an apparatus for examining carcasses with an ultrasound transducer by means of ultrasound, an ultrasound transducer being adapted to come into contact with the surface of a carcass.

The ultrasound transducer in such an apparatus has one or more transducer elements which transmit an ultrasound signal in a known manner whose frequency is typically in the MHz range, and when a transducer element is in contact with a body (e.g. the body of a human or a carcass), the ultrasound signal propagates in the body, where inhomogeneities reflect part of the energy in the ultrasound signal, and part of the reflected energy is received and detected by the transducer element which transmitted the signal, or by other transducer elements which convert the received signal to an electric signal which is processed in a known manner in an apparatus with which the ultrasound transducer is connected. Information on the structures of the body along the propagation path of the ultrasound signals in the body can be derived from the received signals. Information on the internal structures of the body along a plurality of propagation paths can be obtained by moving the ultrasound transducer across the surface of the body in a known manner, and these items of information can be combined in a known manner to two-dimensional images which represent the internal structures of the body.

The object of the invention is to provide an apparatus for examining carcases by means of ultrasound with a view to obtaining such information as can form the basis for i.a. grading of carcasses. Carcasses are traditionally graded on the basis of amount of meat, distribution of meat and fat, etc.

Devices for grading of carcasses are known wherein probes are inserted at well-defined locations on the surface of the carcasses, the distribution of meat and fat in the insertion direction of the probe being measured in these positions. This requires rather comprehensive and expensive equipment, which just gives measurements in a limited number of positions, causing grading unreliability. Owing to the vulnerability of the probes it is inexpedient and expensive to measure in a large number of positions with such equipment.

The following patent publications teach the use of ultrasound for examination of carcasses: DK 4965/77, DE-A-3 315 513, FR-A-2 545 010, GB-A-2 213 263, U.S. Pat. No. 3,496,764, U.S. Pat. No. 4,785,817 and U.S. Pat. No. 5,079,951. These known devices moreover use either a movable ultrasound transducer which is moved across the surface of a carcass manually or automatically, or use transducers in a water bath in which the carcass is immersed. However, all the devices described in these are either considerably more complicated or more inaccurate than the apparatus of the present invention.

The object of the invention is to provide an apparatus for examining carcasses with a view to i.a. grading of the carcasses. The apparatus is to be compact and sturdy and to be capable of being mounted on most slaughter lines without significant changes in these.

SUMMARY OF THE INVENTION

This object is achieved by an apparatus comprising an ultrasound transducer adapted to come into contact with the surface of a carcass, the ultrasound transducer being mounted immovably on the stationary frame of a slaughter line. Each slaughter line comprises a transport mechanism for advancing carcasses between the various working stations of the slaughter line, and since the ultrasound transducer of the apparatus of the invention is mounted immovably on the frame of the slaughter line, the transport mechanism of the slaughter line moves the carcasses past the ultrasound transducer, which is arranged at an expedient location on the slaughter line so as to create contact between the ultrasound transducer and the carcasses. Traditionally, the ultrasound transducer is moved with respect to the body to be examined, but according to the invention it is the carcasses which are moved with respect to the stationary ultrasound transducer. Since all the carcasses are moved in substantially the same manner, great reproducibility of the measurements is obtained, and the immovably mounted ultrasound transducer therefore does not have to be light to be moved, like in the known systems, but, on the contrary, it may be made sturdy since it is not to be capable of being manipulated in use.

An ultrasound transducer having just a single transducer element may be used, scanning being performed along a single selected line in the movement of the carcase across the transducer element, but, the ultrasound tranducer may advantageously be provided with a plurality of transducer elements arranged immovably along an arcuate curve which is adapted to the curvature of the carcasses, since this enables examination and optionally two-dimensional sectional image formation for each transducer element, since these may be distributed transversely to the carcass advancing direction of the transport mechanism. This makes it possible to examine very large areas of each carcass, and information of a three-dimensional nature can be deduced from the sectional images.

In a preferred embodiment of the invention, the transducer elements of the ultrasound transducer face upwardly, and the transport mechanism of the apparatus is adapted to move carcasses across the ultrasound transducer resting on it with a considerable part of their weight, thereby creating good contact between the transducer elements of the ultrasound transducer and the carcasses.

It is expedient to arrange the apparatus of the invention on a slaughter line immediately after the dehairing device and the gambreling table, since the carcasses, precisely at this location, have had their hair removed and have been given a wet and smooth surface which lends itself for examination by means of ultrasound. This location on the slaughter line is appropriate, because the carcasses arrive from the dehairing device in a horizontal position on the gambreling table, and the transport mechanism of the slaughter line then lifts the carcasses hanging in the hind legs and move them further on for singeing, so that examination by means of ultrasound is no longer expedient. Therefore, the apparatus of the invention may advantageously be provided precisely at this location on the slaughter line, where the transport mechanism lifts the carcasses from the lying state to the hanging state at a controlled and fairly even rate, since this is the only location on the slaughter line where the carcasses are advanced in their longitudinal direction, the carcasses being scanned along the back starting at their tail end and terminating at the neck.

To direct the carcasses across the ultrasound transducer, the apparatus may have a chute which defines a guide path across the ultrasound transducer, said ultrasound transducer and said chute having cross-sections transversely to the direction of feed which correspond to each other without necessarily being identical. To ensure good contact between the transducer elements of the ultrasound transducer and the carcasses during feeding on the chute, the ultrasound transducer may advantageously protrude or form a constriction of the feed path, since this provides well-defined deformation of the carcases, resulting in a well-defined contact pressure.

BRIEF DESCRIPTION OF THE DRAWINGS

A preferred embodiment of the invention is described below with reference to the drawing, in which.

DETAILED DESCRIPTION OF THE INVENTION

Figure 1:
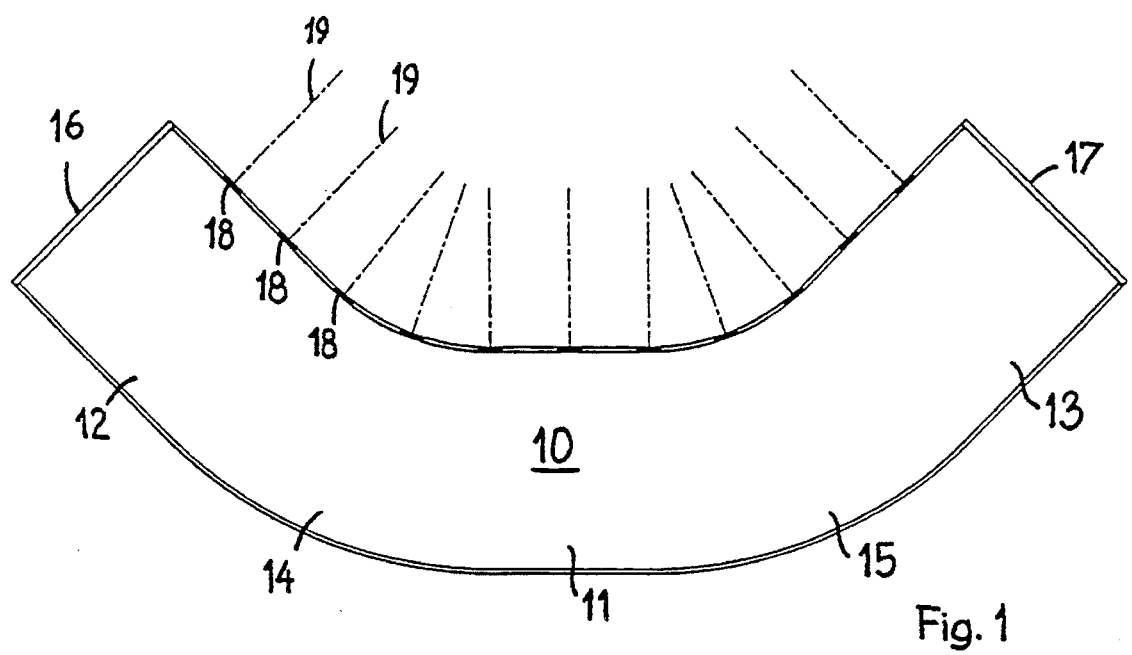
FIG. 1 is a vertical section through an ultrasound transducer.
Figure 2:
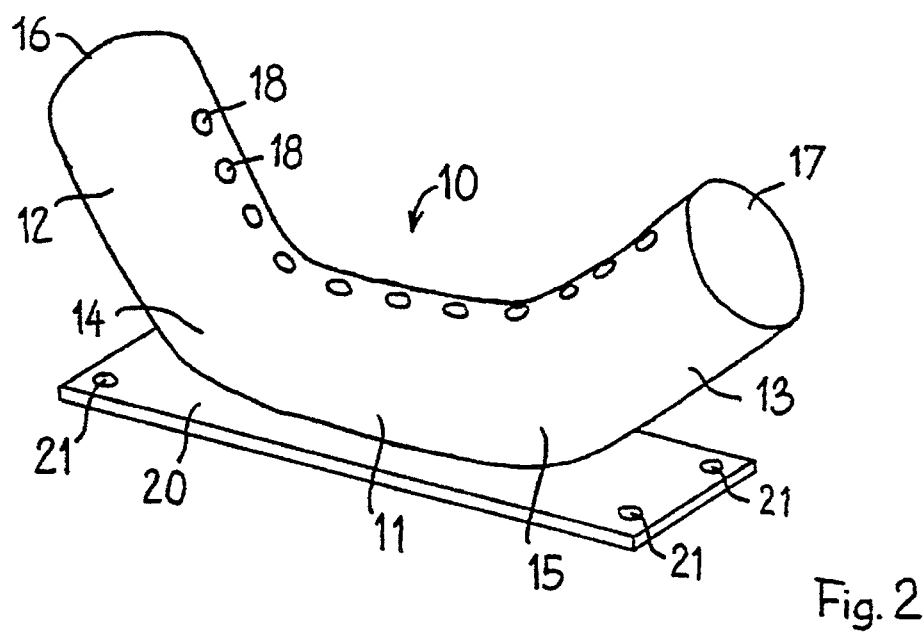
FIG. 2 is a perspective view of the ultrasound transducer of FIG. 1.

FIGS. 1 and 2 show an ultrasound transducer in the form a pipe having a circular cross-section whose diameter is here about 100 mm. The ultrasound transducer 10 has a horizontal central part 11 and two lateral parts 12 and 13, each of which forms an angle of 45° with the horizontal central part. Each of the lateral parts 12 and 13 is connected with the horizontal central part 11 by concave portions 14 and 15. The ultrasound transducer 10 thus forms a curved or hanger shaped pipe member which is closed at the ends 16, 17 and has its concave side facing upwards. The upwardly directed face of the ultrasound transducer has a plurality of transducer elements 18 along the ultrasound transducer in positions which each correspond to the highest point on the cross-sectional curve of the pipe at the location in question, and these transducer elements 18 are connected in a known manner (not shown) to an apparatus capable of applying electric signals to the transducer elements 18 such that these are caused to oscillate at an ultrasound frequency. When the transducer element 18 is in contact with a medium, such as e.g. a carcase which can transmit ultrasound signals, ultrasound signals will propagate from respective transducer elements 18 along sound propagation directions 19 which are located in the medium. Each transducer element 18 is adapted to receive reflected or scattered ultrasound signals from the medium likewise in a known manner, which arrive at the transducer element from the medium along respective propagation directions 19.

FIG. 2 shows the ultrasound transducer 10 mounted on a plate 20 to which it is e.g. welded or bolted. The plate 20 is provided with a plurality of holes 21 so that the plate 20 with the ultrasound transducer 10 can be secured immovably and in the shown position on the stationary frame of a slaughter line by means of bolts through the holes 21.

Figure 3:
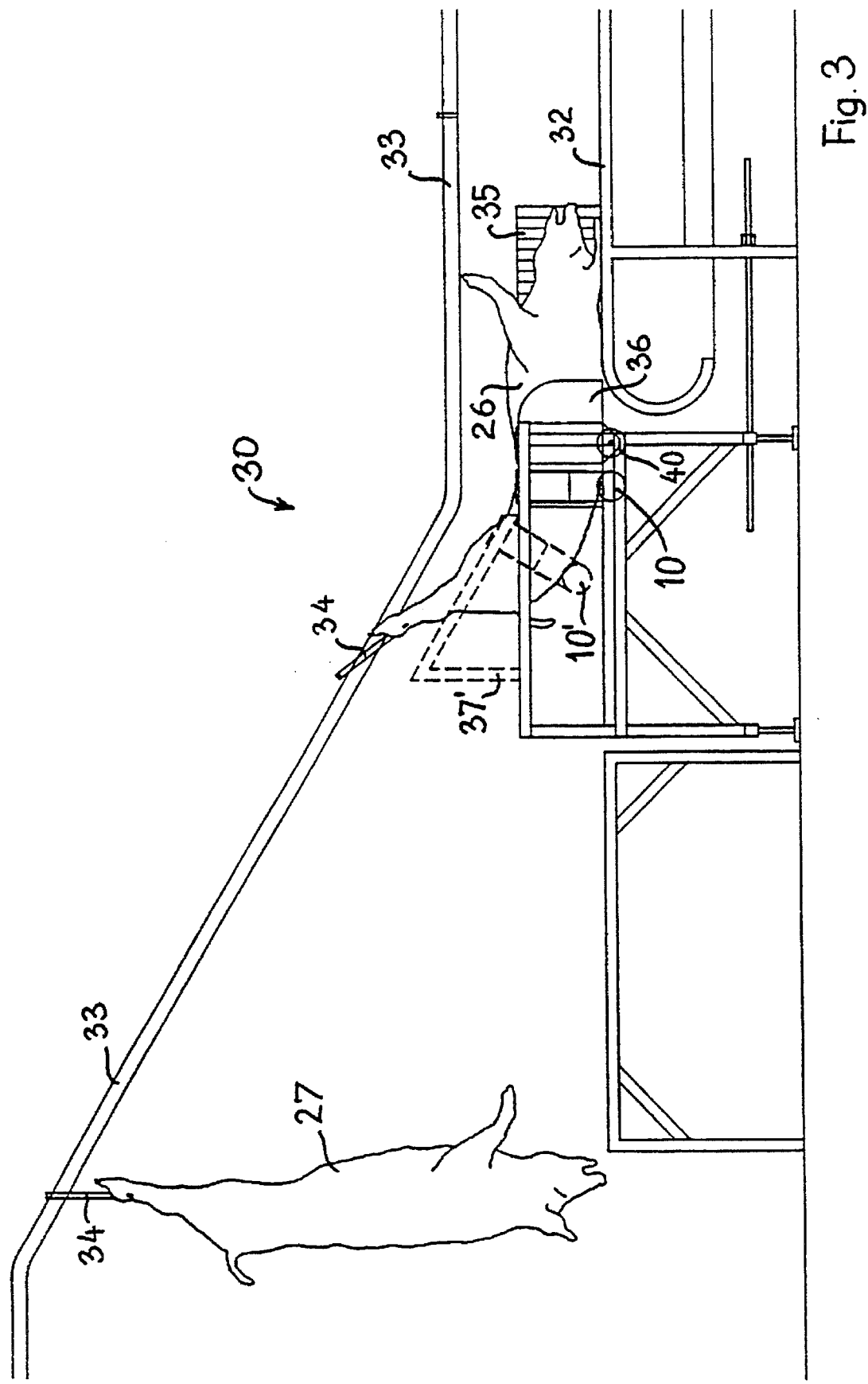
FIG. 3 is an elevational view of a slaughter line in which the invention is employed.
Figure 4:
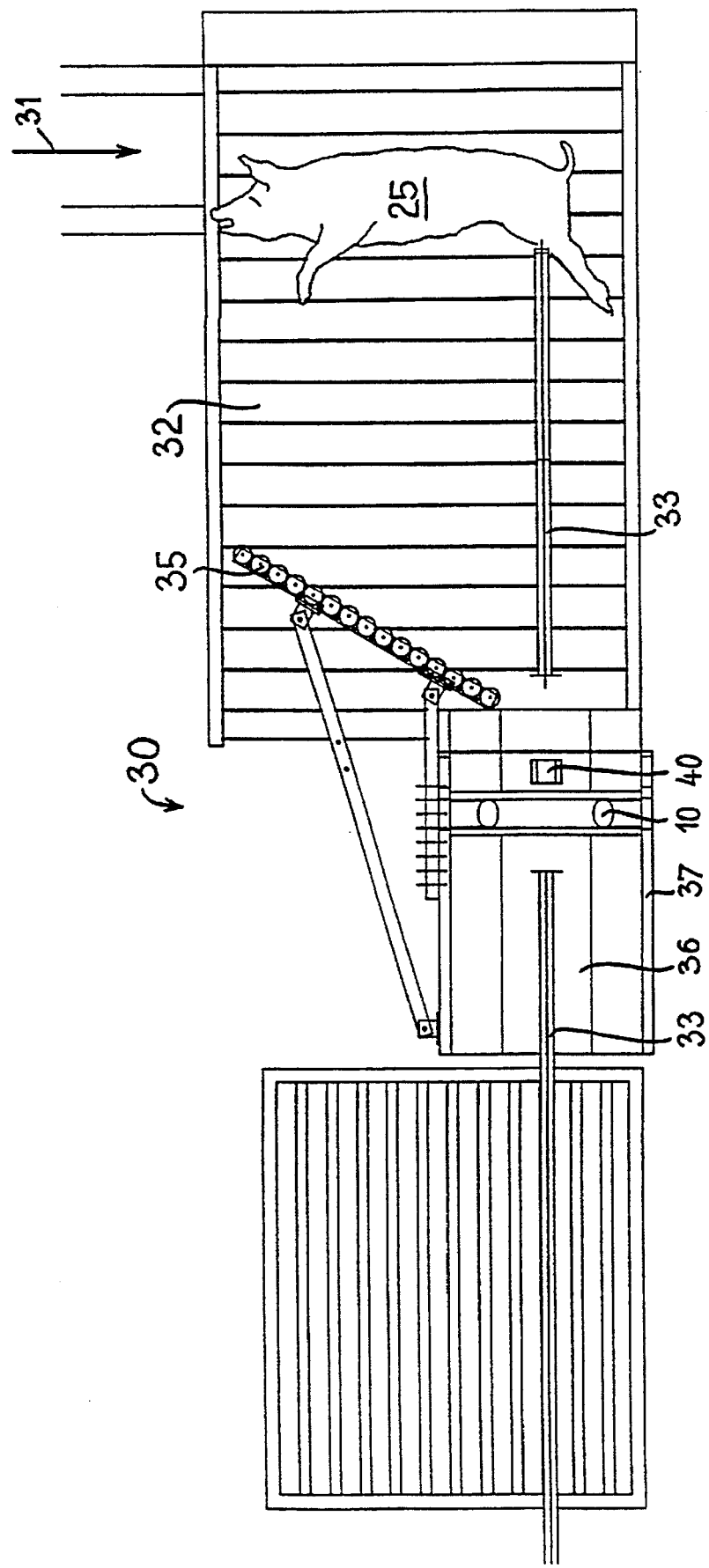
FIG. 4 is a top view of the slaughter line of FIG. 3.

FIGS. 3 and 4 show part of a slaughter line 30. A carcass 25 has been moved from the dehairing device (not shown) of the slaughter line in a direction indicated by a arrow 31, and in FIG. 4 it is shown lying on the gambreling table 32 of the slaughter line. The carcass has had all its hair removed in the dehairing device, and its surface is here wet and smooth so as to provide acoustic contact with the ultrasound transducer 10 (vide infra).

The slaughter line has a conveyor means or carcass transport mechanism for moving a carcass across the ultrasound transducer so that the ultrasound transducer comes into contact with a surface of carcass. As embodiment, this mechanism includes a slide rod 33 which is suspended from the ceiling. Above the gambreling table 32, the slide rod 33 is arranged at a low height, said slide rod 33 being arranged at a height in the rest of the slaughter line via a rising section such that carcasses 27 are transported in a hanging state through the slaughter line. Lying on the gambreling table, the carcasses have the hind legs pierced by a hook-shaped gambrels 34, following which the transport mechanism pulls the carcasses in a direction to the left on the gambreling table 32 with the hind legs first by means of the gambrels 34.

A guide plate 35 guides the carcasses to a path 36 for positioning the carcasses in their transverse direction. The path 36 is a chute or a trough-shaped path having an upwardly open cross-section which corresponds to the cross-section of the ultrasound transducer 10, as appears from the FIG. 1. The ultrasound transducer 10 is here arranged such that a portion of the chute-shaped path 36 is present both upstream and downstream of the ultrasound transducer 10, and, as appears from FIG. 3, the ultrasound transducer 10 is arranged such that the upper side of the horizontal central part 11 of the transducer protrudes slightly more upwards than the internal base of the path 36. The path 36 moreover has a cross-section which is slightly more open than the cross-section of the ultrasound transducer 10.

FIG. 3 shows how a carcass is moved from the gambreling table 32 by the pull from a gambrel 34 into the trough-shaped path 36 with the back downwards and the hind legs forwards in the direction of movement. The carcass 26 is hereby moved across the ultrasound transducer 10, lying on it with part of its own weight. Since the ultrasound transducer 10 constitutes a constriction of the cross-section of the guide path 36, it is ensured that the ultrasound transducer 10 is in good contact with the surface of the carcass at any time. The height of the ultrasound transducer 10 with respect to the guide path 36 can be adjusted as needed with a view to regulating the part of the weight of the carcass which rests on the ultrasound transducer.

At this location the ultrasound transducer is secured immovably to a stationary frame 37 of the slaughter line.

An ultrasound transducer 10' is shown in FIG. 3 in an alternative position in which it is inclined and is secured immovably to the stationary frame 37' of the slaughter line.

By means of the arrangement shown here a carcass is moved across the ultrasound transducer 10 on which the carcass rests with part of its own weight, and the carcass is examined in its entire length from tail to neck, said transport mechanism conveying the carcass in their longitudinal direction from a lying state to a vertically hanging state, which is illustrated by a carcass 27 which is moved to the next station of the slaughter line in which singeing of the carcasses is performed.

For the image formation by means of ultrasound to be consistent and accurate, it is required in the arrangement described above that the carcasses are fed across the ultrasound transducer at a constant rate by means of the transport mechanism. If this is not the case, the slaughter line may be provided with an encoder 40 of a known type, which is arranged in connection with the chute-shaped path 36 and in the vicinity of the ultrasound transducer 10. The encoder 40 may have a wheel in a known manner, which rotates when the carcass 26 moves across the wheel, and the encoder 40 then applies pulses in step with the feed in a known manner. These pulses are used for synchronization of the ultrasound signals from the transducer elements 18 so as to create an umambigous connection between the formed ultrasound images and the corresponding positions in the carcass. The use of a stiff ultrasound transducer 10 having several transducer elements 18 moreover enables consistent and true measurements transversely to the carcasses.

Figure 5:
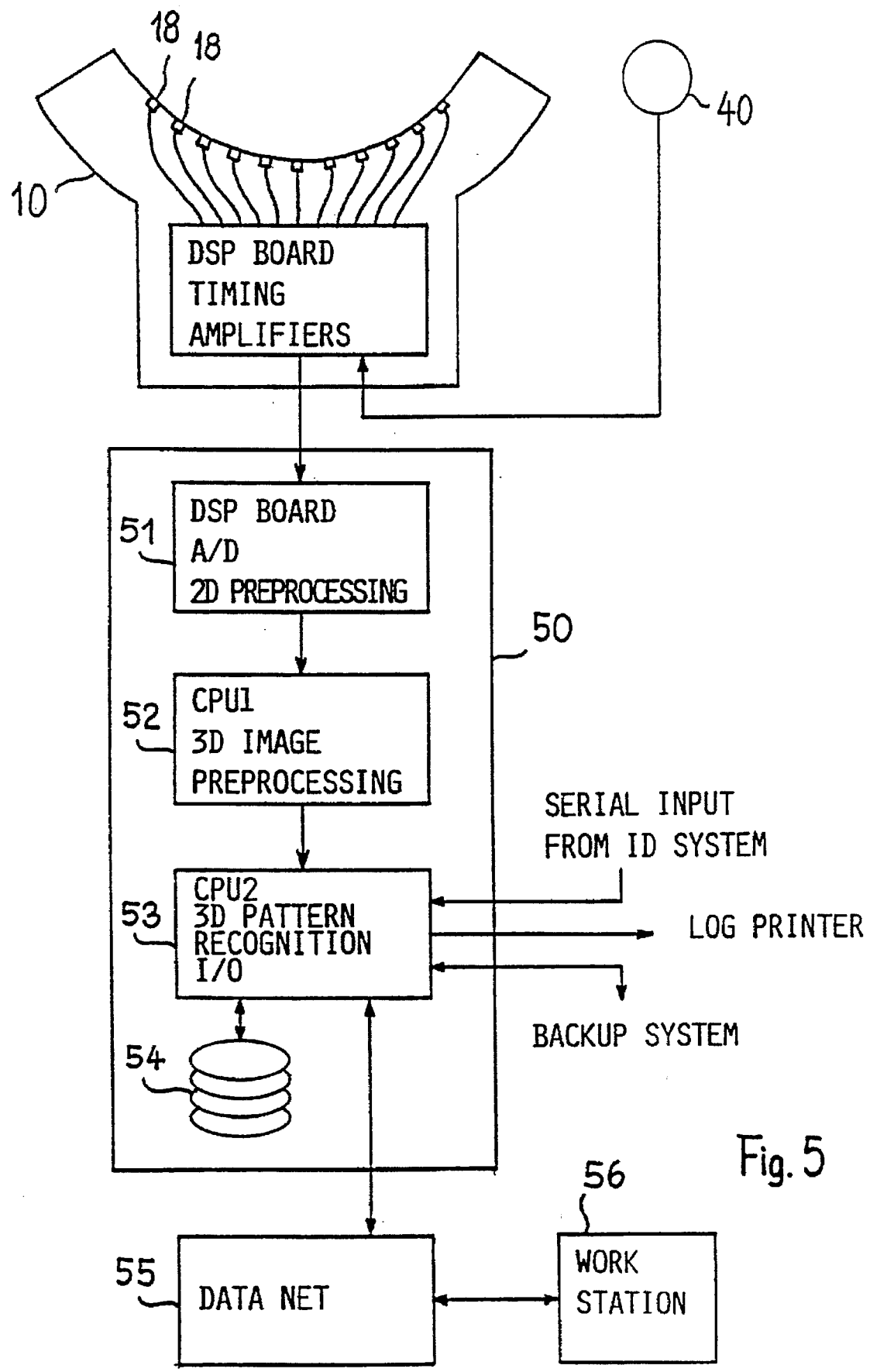
FIG. 5 is a schematic view of a complete system for grading carcases according to the invention.

FIG. 5 shematically shows a complete diagram of a complete system for grading of carcasses, in which the transducer 10 is connected to a data processing system. The transducer 10 is here shown in an alternative embodiment in which it consists of a circular ring sector having a thickness of about 100 mm and an internal radius of about 200 mm. The internal radius is selected here so that it is suitable for examination of hog carcasses. For examination of carcasses of other animal breeds, e.g. sheep or cattle, a transducer 10 may be manufactured whose internal radius is smaller or larger, respectively, than for hog carcasses. The transducer 10 here has eleven transducer elements 18 equidistantly distributed on a circular arc of said internal radius and positioned so as to point to the center of the circular ring sector of the transducer. This embodiment gives both a good physical adaptation to the shape of the carcasses and an even distribution of the total "field of vision" of the transducer 10.

All the transducer elements 18 are connected to a digital signal processor (DSP) which, together with a multiplexer, pulse transmitters and analog signal conditioning circuits is positioned immediately below the transducer elements and contained in one of the same box of stainless metal. The metal box, closed completely in practice, provides optimum shielding of the relatively weak electric echo signals from the transducer elements 18. The incorporated DSP provides for the detailed sequence control and timing in connection with excitation of the transducer elements 18 and the collection of echo data. The encoder 40 is connected to the electric circuits in the transducer 10 via a cable, and these circuits are electrically connected to a computer 50 to which ultrasound signals are transmitted as multiplexed analog signals of video level (about 1 V).

The first stage in the computer 50 is a DSP board, which converts the received analog echo signals to digital echo data, which are gathered in respective data packets for each cross-sectional image. These data packets are transmitted to a first CPU 52 which builds and preprocesses a three-dimensional image of the carcass on the basis of the two-dimensional data packets. The preprocessed three-dimensional image is transmitted to a second CPU 53 which interpretes the preprocessed three-dimensional image using a pattern recognition technique. The second CPU 53 generates the desired data concerning the total meat per cent of the carcass, the meat percentages for each individual one of the major cuts of the carcass, such as ham, middle and fore-end, as well as thickness distribution of the fat layer, the size and shape of muscles, content of intramuscular fat in certain muscles, etc. The second CPU 53 communicates with a hard disc 54 and peripheriral units in the form of a display unit for identification of the gambrels 34 of the carcass concerned (e.g. via a radio transponder), a log printer and optionally a manual backup system for classification. Finally, the second CPU 53 also communicates with an outer data network 55, which is partly used for transmitting the measurement results to the computer system of the slaughter house and partly for communication with a graphic work station 56, which are also the user's interfaces to the computer 50. The data network is also useful for transmitting information for the control of future automatic slaughter machinery, which is controlled on the basis of anatomical information generated from ultrasound data which have been collected by means of the shown system.

Most slaughter lines have the configuration mentioned here, where the carcasses leave the dehairing device of the slaughter line lying horizontally on a gambreling table, and are then directly moved along the slide rod of a transport mechanism for singeing, and the ultrasound transducer can consequently be provided at the shown location in most slaughter lines where the carcasses are transferred from a lying state to a hanging state. The movement hereby performed by the carcasses is utilized by the apparatus of the invention for creating mutual movement between the stationary ultrasound transducer 10 and the carcasses.

It will be seen that a very huge amount of data can be obtained hereby with simple means, containing accurate and consistent information on the internal structures of the carcases measured in their entire longitudinal direction as well as transversely to the carcass. It is then possible by means of computer programs to oriente oneself completely and unambiguously in this huge amount of data, since e.g. specific bones can easily be identified and form the basis for orientation in the amount of data. The collected amount of data form a whole, and it is therefore possible to orient oneself completely and unambiguously in images in longitudinal section as well as cross-section and combinations thereof, also even if the carcasses when being fed are in an oblique position or change their position en route. Hereby, almost complete anatomic measurements of the carcasses can be obtained, in particular a measurement and grading of the individual piece of meat, where not only the size and weight of the piece of meat are measured, but also the content and distribution of intramuscular fat of the piece of meat. Further, it is possible to detect abscesses and suffusion, which are difficult to detect by traditional measurement and grading equipment.

The setup in FIGS. 3 and 4 can be expanded in a simple manner by equipment making it possible also to determine the sex of the carcasses. The carcasses are fed as shown with the hind legs separated and pointing forwardly in the direction of feed. An extra ultrasound transducer can be mounted on a movable arm so as to protrude between the hind legs of the carcase and to scan the region in which the genitals are positioned. When the carcasses are advanced further these push the extra transducer aside, and in no way does it interfere with the measurement, as mentioned above.

I claim:

1. An apparatus for examining carcasses comprising an ultrasound transducer and a conveyor means for moving a carcass across the ultrasound transducer so that the ultrasound transducer comes into contact with a surface of the carcass, the ultrasound transducer and the conveyor means being arranged with respect to each other such that as the conveyor means moves the carcass across the ultrasound transducer, a considerable part of the weight of the carcass being examined rests on the ultrasound transducer.

2. The apparatus of claim 1, wherein the ultrasound transducer comprises a plurality of ultrasound transducer elements arranged immovably along an accurate curve, said elements facing inwardly toward the curvature of the curve.

3. The apparatus of claim 2, wherein the curve of the ultrasound transducer faces upwards, the conveyor means for the carcasses being arranged with respect to the ultrasound transducer so that a carcass is moved across the upwardly facing ultrasound transducer.

4. The apparatus of claim 3, including a chute having a cross-section corresponding to the curvature of the ultrasound transducer, said chute defining a guide path for guiding a carcass across the ultrasound transducer.

5. The apparatus of claim 4, wherein the lowest point of the curvature of the ultrasound transducer that contacts the carcass protrudes further upwards than a corresponding adjacent area of the chute.

6. The apparatus of claim 4, wherein the curvature of the ultrasound transducer is more constricted than the chute.

7. A slaughter line comprising the examining apparatus of claim 1 and a dehairing device, the examining apparatus being arranged downstream of the dehairing device.

8. The slaughter line of claim 7, including a singeing device, the examining apparatus being arranged upstream of the singeing device.

9. The slaughter line of claim 7, wherein the conveyor means moves a carcass across the ultrasound transducer longitudinally of the longitudinal length of the carcass and with the back of the carcass being toward the ultrasound transducer.

* * * * *